United States Patent [19]
Cole

[11] Patent Number: 5,749,913
[45] Date of Patent: May 12, 1998

[54] SYSTEM AND METHOD FOR COLLECTING AND STORING ELECTROTHERAPY DATA ON A DETACHABLE MEMORY DEVICE

[75] Inventor: Clinton S. Cole, Seattle, Wash.

[73] Assignee: Heartstream, Inc., Seattle, Wash.

[21] Appl. No.: 649,414

[22] Filed: May 16, 1996

Related U.S. Application Data

[63] Continuation-in-part of Ser. No. 314,395, Sep. 28, 1994, Pat. No. 5,549,115.

[51] Int. Cl.[6] ............................................. A61N 1/37
[52] U.S. Cl. ............................................................. 607/59
[58] Field of Search ..................................... 607/59, 60

[56] References Cited

U.S. PATENT DOCUMENTS

| | | |
|---|---|---|
| 4,250,888 | 2/1981 | Grosskopf . |
| 4,642,769 | 2/1987 | Petrofsky ............................. 607/60 |
| 4,715,385 | 12/1987 | Cudahy et al. . |
| 4,919,139 | 4/1990 | Brodard ............................. 607/59 |
| 4,926,865 | 5/1990 | Oman ............................. 607/59 |
| 5,002,062 | 3/1991 | Suzuki . |
| 5,033,469 | 7/1991 | Brodard ............................. 607/59 |
| 5,228,450 | 7/1993 | Sellers . |
| 5,333,616 | 8/1994 | Mills et al. . |
| 5,334,030 | 8/1994 | Brilliott . |
| 5,338,210 | 8/1994 | Beckham et al. . |
| 5,345,367 | 9/1994 | Pierce et al. . |

FOREIGN PATENT DOCUMENTS

| | | |
|---|---|---|
| 3 221 399 A1 | 12/1983 | Germany . |
| 4 337 110 C1 | 11/1994 | Germany . |
| A 6-036098 | 2/1994 | Japan . |
| 2 225 495 | 5/1990 | United Kingdom . |

OTHER PUBLICATIONS

U.S. Patent Application No. 08/227,553, "Electrotherapy Method and Apparatus" filed Apr. 14, 1994.
U.S. Patent Application No. 08/240,272 "Defibrillator with Self-Test Features" filed May 10, 1994.
Operating instructions for Laerdal Heartstart Medical Control Unit with Multiplex Tape Format.
Marquette® Responder™ 1500 Defibrillator and cardiac care system operator's manual (16th Ed.) (1994).

*Primary Examiner*—William E. Kamm
*Attorney, Agent, or Firm*—James R. Shay; Cecily Anne Snyder

[57] ABSTRACT

A method of operating an electrotherapy device that provides advantages over prior art approaches. In one embodiment, the electrotherapy device stores collected information in a detachable memory device and uses a clock within the memory device to associate a time information with the electrotherapy information. The time information is useful for producing later reports or displays of the collected information by the electrotherapy device or by another device to which the detachable memory device has been attached. The invention is also an electrotherapy system including: an electrotherapy device, the electrotherapy device including a memory device port; and a memory device, the memory device including a connector adapted to be connected to the electrotherapy device memory port, a clock, and a digital memory.

12 Claims, 4 Drawing Sheets

SYSTEM AND METHOD FOR COLLECTING AND STORING ELECTROTHERAPY DATA ON A DETACHABLE MEMORY DEVICE

This application is a continuation-in-part of U.S. patent application Ser. No. 08/314,395 for "Method and Apparatus for Gathering Event Data Using a Removable Data Storage Medium and Clock," filed Sep. 28, 1994, now U.S. Pat. No. 5,549,115, issued 27 Aug. 1996, the disclosure of which is hereby incorporated by reference.

BACKGROUND OF THE INVENTION

This invention relates to electrotherapy devices, such as defibrillators, cardioverters and pacers, and detachable memory units for those devices. In particular, the invention relates to the use of detachable memory units to which electrotherapy devices can write event and time information and from which such information may be later retrieved.

Electrotherapy devices are used to provide electric shocks to treat patients for a variety of heart arrhythmias. For example, external defibrillators provide relatively high-energy shocks to a patient, usually through electrodes attached to the patient's torso, to convert ventricular fibrillation to a normal sinus rhythm. Similarly, external cardioverters can be used to provide shocks to convert atrial fibrillation to a more normal heart rhythm. In this application, the term "electrotherapy device" includes devices performing only a monitoring function.

Event data means information that can be related to particular intervals of time. The time intervals may be "elapsed time," i.e., time related to a reference event, such as power-up of the data collecting device or start of the data collection process. The time intervals may instead be synchronized with a master standard, such as Greenwich mean time or an arbitrarily selected timekeeper, in which case the time is known as "synchronized time." Accepted time units (seconds, minutes, etc.) are used to measure both elapsed time and synchronized time.

One example of event data is an electrocardiograph showing a patient's heart electrical activity, which may be plotted versus elapsed time from a starting or triggering event. Event data also includes the raw data upon which the plots or graphs are based, whether in digital, analog or any other form. The event data may be a continuous data stream, a discontinuous series of events, or a combination of continuous data and discrete events.

Prior art electrotherapy devices record event information and time information collected from the patient, reported by the device and/or otherwise collected from the devices' surroundings (such as audio information, including the voices of the devices' operators) during the operation of the device. This and other information collected by an electrotherapy device may be referred to collectively as "electrotherapy information". For example, the Laerdal Heartstart 3000 external defibrillator records patient ECG and information about the defibrillator in a solid state memory module. This patient and ECG information can be later retrieved from the memory module using suitable software. As another example, the Marquette Responder 1500 external defibrillator stores event data such as patient ECG on a data card inserted into a data card slot in the defibrillator. The event and time data regarding the patient's physiological condition may be logged to provide information to later caregivers about the patient and about the care the patient received, such as the time required for the emergency medical technicians to reach the patient and the patient's response to the treatment.

Event data collected from electrotherapy devices may be analyzed to extract useful time-based information. Part of the event data analysis often requires reference to a local clock by the data user to place the time stamped on the collected event in the context of the data user's time. For example, if a portion of the collected event indicates that the event occurred at 4:00 PM, the data user must assume that the electrotherapy device clock and the data user's local clock indicated "4:00 PM" at the same time. In other words, the data user must assume that the electrotherapy device clock and the data user's local clock are synchronized. In addition, the data user must assume that the electrotherapy device's measure of a second or a minute is the same as the data user's local measure of a second or a minute so that the recorded time (whether elapsed time or synchronized time) may be interpreted in a meaningful way.

The synchronized time indicated by a device's clock may drift from the synchronized time indicated by the master timekeeper because of environmental conditions, mechanical problems, or other reasons. Also, the act of setting the electrotherapy device clock could introduce discrepancies between the time indicated by the device's clock and the time indicated by the data user's clock, especially if the data logger clock is set by hand, or if the electrotherapy device's clock was not initially synchronized to the data user's clock prior to event data collection. These problems are compounded if a single data user receives event data from multiple electrotherapy devices, since each electrotherapy device clock may have been affected in different ways by environmental conditions, errors in initial setting, and the like. Thus, when the accurate logging of synchronized time is important, a relatively expensive clock and elaborate and/or expensive time setting procedures may have to be included in the electrotherapy device.

SUMMARY OF THE INVENTION

This invention is a method of operating an electrotherapy device that provides advantages over prior art approaches. In one embodiment, the electrotherapy device stores collected information in a detachable memory device and uses a clock within the memory device to associate a time information with the electrotherapy information. The time information is useful for producing later reports or displays of the collected information by the electrotherapy device or by another device to which the detachable memory device has been attached.

The electrotherapy information may be collected automatically or entered manually. In a preferred embodiment, the memory device is a PC data card. The invention may also include a step of identifying a detachable memory device attached to the electrotherapy device, the storing step comprising storing the electrotherapy information and the time information on the detachable memory device.

In one embodiment, wherein the memory device comprises a digital memory, the method includes erasing a section of the digital memory prior to the storing step. In another embodiment, wherein the memory device comprises first and second digital memories, the method includes erasing the first digital memory and the storing step includes storing electrotherapy information and time information in the second digital memory during the erasing step.

The invention is also an electrotherapy system including: an electrotherapy device, the electrotherapy device including a memory device port; and a memory device, the memory device including a connector adapted to be connected to the electrotherapy device memory port, a clock, and a digital memory. The invention may also include means for using the clock to associate time information with electrotherapy information collected by the electrotherapy device. In another embodiment, the memory device also includes an identifier, with the electrotherapy device further including means for identifying a memory device connected to the memory port. In yet another embodiment, wherein the digital memory is a first digital memory, the memory device further includes a second digital memory, with the electrotherapy device further including means for erasing the first digital memory while storing electrotherapy information and time information in the second digital memory.

The invention is described in more detail below with reference to the drawings.

DETAILED DESCRIPTION OF THE PREFERRED EMBODIMENTS

Figure 1:
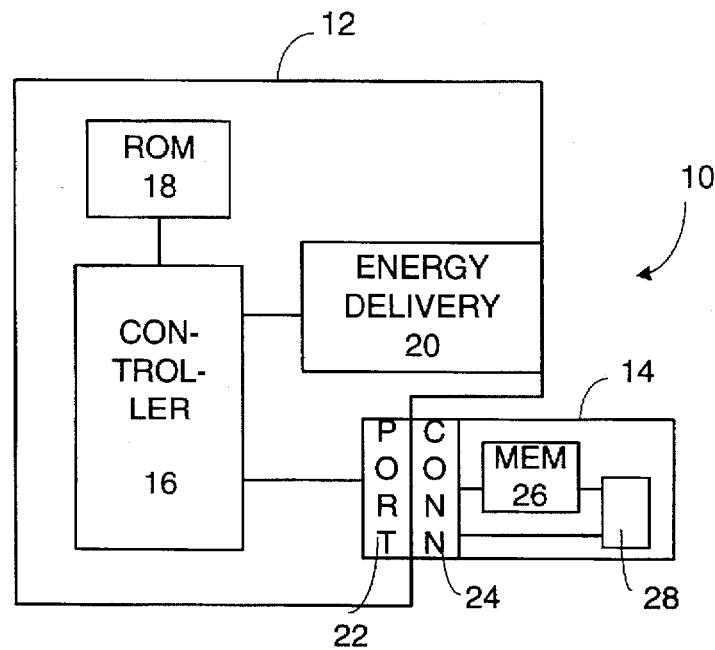
FIG. 1 is a block diagram of an electrotherapy system according to one embodiment of this invention.

FIG. 1 is a block diagram of an electrotherapy system according to one embodiment of this invention. Electrotherapy system 10 includes an electrotherapy device 12 connected to a memory device 14. Electrotherapy device 12 may be an external defibrillator, an external cardioverter, an external pacer, or any other electrotherapy device. A controller 16 within electrotherapy device 12 operates the device according to software instructions contained within device ROM (Read Only Memory) 18. It should be understood that, in this and other embodiments described below, "controller" means a microprocessor, controller, gate array, other control logic, or any combination of these elements.

The electrotherapy device operating modes can include patient treatment (in which, e.g., a therapeutic pulse is delivered to a patient via energy delivery and monitoring module 20), monitoring (in which, e.g., the patient's ECG is monitored through module 20) and self-test mode (in which device 12 runs self-test procedures to determine its operating condition).

In any of its operating modes, electrotherapy device 12 can communicate event data with memory device 14 via memory port 22, which communicates with a digital memory 26 within memory device 14 via a connector 24. Electrotherapy device 12 also communicates with a clock 28 in memory device 14 through connector 24. Clock 28 provides time information for association with the event data from electrotherapy device 12, as discussed below.

During operation in patient treatment mode, electrotherapy device 12 may collect event information relating to the patient (such as patient ECG) and event information relating to the device itself (such as the charging of energy delivery and monitoring module in preparation for a shock or the delivery of the shock itself). Controller 16 transmits this event information to digital memory 26 in memory device 14. In addition, controller 16 associates time information taken from clock 28 with the event data and stores the associated time information in digital memory 26 as well.

During operation in monitoring mode, electrotherapy device 12 may collect and record patient information and its associated time without providing any treatment to the patient. The electrotherapy device may also record device event information and its associated time as well.

During operation in self-test mode, electrotherapy device 12 performs self-test and/or self-calibration procedures either automatically or on demand. Further information on self-test and calibration procedures for electrotherapy devices may be found in copending U.S. patent application Ser. No. 08/240,272, "Defibrillator With Self-Test Features," filed May 10, 1994, the disclosure of which is incorporated herein by reference. The controller may store the results of the self-tests and/or calibrations in digital memory 26 along with associated time information taken from clock 28.

Event data collected by the electrotherapy device 12 and stored in memory device 14 may be used later in a location, such as a hospital, which is physically distant from the initial treatment location. Memory device 14 can be separated from electrotherapy device 12 and connected to a main data recovery unit (such as a computer) in the hospital or other location through appropriate connectors. In this way, the event data is available for later diagnosis and treatment, and the electrotherapy device itself remains available for use in the field.

The clock 28 used by the electrotherapy device to associate time information with the ECG, defibrillator operating condition, and/or other event data will be connected to the main data recovery unit along with the digital memory. This step permits a comparison between the clock 28 and a main clock within the main data recovery unit so that the electrotherapy device event data can be associated with synchronized time. This comparison can be used to determine whether synchronized time indicated by the memory device clock (i.e., the time associated with the recorded event data) differs from the synchronized time standard shown by the main data recovery unit. In addition, the ability to connect the memory device clock and the main clock permits time synchronization of the electrotherapy device prior to use in the field and correction for any clock drift after use in the field through interpolation or any other known technique. Furthermore, this system permits multiple electrotherapy devices to synchronize their clocks with a single main clock and to transfer or copy their collected event data into a single data recovery unit. The event data gathered by each will eventually be recovered in a single place and will be synchronized to a single time source.

In an alternative embodiment, a clock within the electrotherapy device is used together with clock 28 to associate time information with the electrotherapy event data.

Each electrotherapy device may uniquely identify the data it gathers so that the main data recovery unit will be able to distinguish event data gathered from one instrument from other event data. This data identification may be done in any manner known in the art.

This invention can be used to learn valuable information regarding emergency medical response times. Since the memory device clock used with each electrotherapy device is each synchronized to the clock in the main data recovery unit, the main data recovery unit can accurately calculate the time between dispatch (if the dispatch clock is synchronized to the main data recovery unit clock) and use of the electrotherapy device to treat a patient. The calculated response times for each electrotherapy device can be accurately compared, since each electrotherapy device clock is synchronized to the same recovery unit clock. The invention also eliminates the need for a technician to periodically set a reference time source (such as his or her watch) from the main clock and visit all of the remote electrotherapy device sites in order to keep all of the instrument clocks in the system synchronized.

Preferred embodiments of this invention are described below with reference to external defibrillators. It should be understood that the invention also relates to other electrotherapy devices as well.

Figure 2:
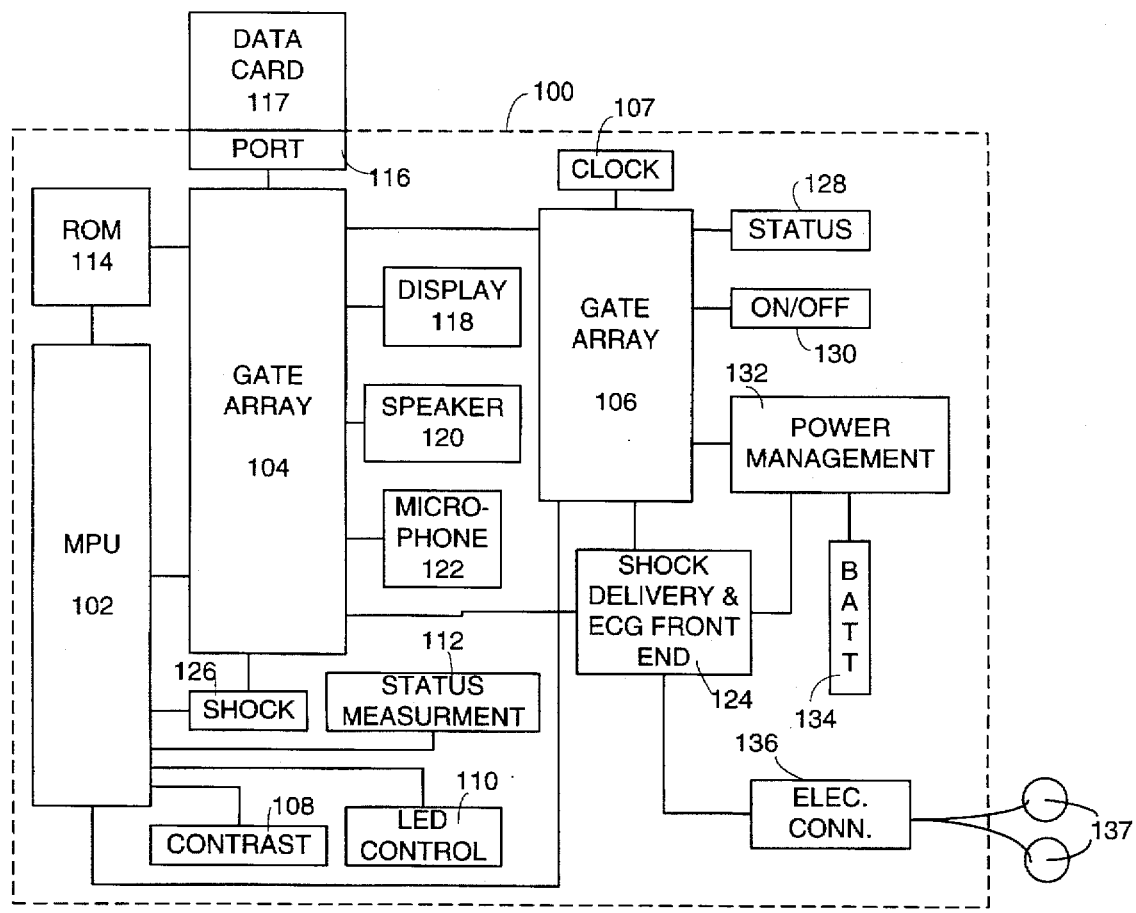
FIG. 2 shows the major components of a semi-automatic external defibrillator according to a preferred embodiment in block diagram form.

The major components of a semi-automatic external defibrillator according to a preferred embodiment are shown in FIG. 2 in block diagram form. Defibrillator control functions are divided among a microprocessor unit (MPU) 102 and two custom gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114, data card port 116 and other system memory elements. System ROM 114 is preferably flash ROM, although EPROM or any other electrically erasable and programmable nonvolatile memory could be used. Data card port 116 is preferably a data card slot configured to interface with PC data cards conforming to the 1995 PC Card standard.

For purposes of writing to a data card, gate array 104 provides the interface and control between defibrillator 100 and a data card 117 attached to data card port 116. For example, gate array 104 contains a FIFO buffer to compensate for differences between the speed with which ROM 114 can be accessed by MPU 102 and the speed with which the memory portion of data card 117 can be accessed. Gate array 104 also controls a display 118, a speaker 120, and a microphone 122. Gate array 104 can actuate a relay within the shock delivery and ECG front end system 124 in response to actuation of a shock button 126 by a user during treatment mode.

Gate array 106 receives time information from clock 107. Gate array 106 also provides a system monitor function by performing automatic self-tests of the defibrillator and its components. The gate array 106 displays the operational status of the defibrillator on a status display 128. Details of suitable self-tests may be found in copending U.S. patent application Ser. No. 08/240,272, "Defibrillator With Self-Test Features," filed May 10, 1994, the disclosure of which is incorporated herein by reference. The results of the self-tests may be stored as time-correlated event data in system memory and/or in data card 117. Gate array 106 is also the defibrillator's interface with a user-activated on/off switch 130.

Gate array 106 controls the power management subsystem 132 to provide power to operate system components from battery 134 and to provide energy to the shock delivery system's capacitor(s) for a therapeutic shock during treatment mode. Gate array 106 also interfaces with the defibrillator's ECG front end 124, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in copending U.S. patent application Ser. No. 08/103,837, "Electrotherapy Method and Apparatus," filed Aug. 6, 1993, and Ser. No. 08/227,553, "Electrotherapy Method and Apparatus," filed Apr. 14, 1994, the disclosures of which are incorporated herein by reference.

These defibrillator components communicate with each other over suitable communication buses, as shown.

Figure 3:
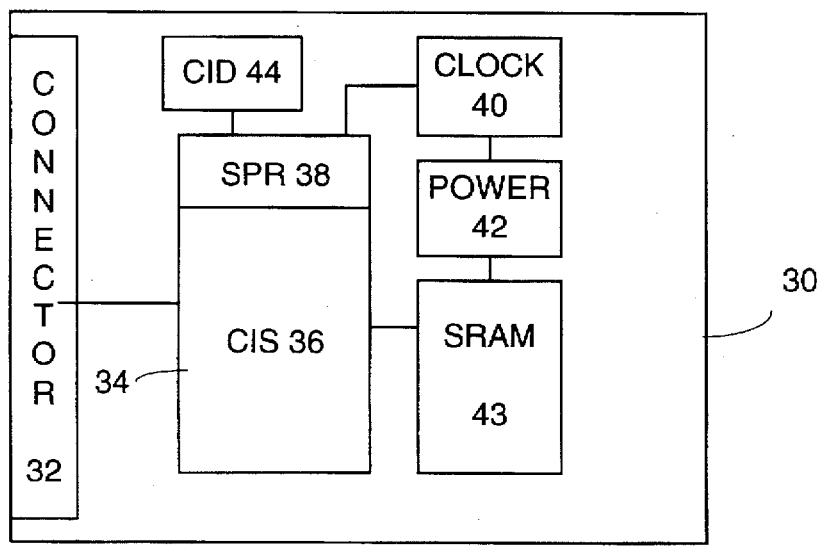
FIGS. 3 and 4 show suitable patient data cards for use with the defibrillator shown in FIG. 2.
Figure 4:
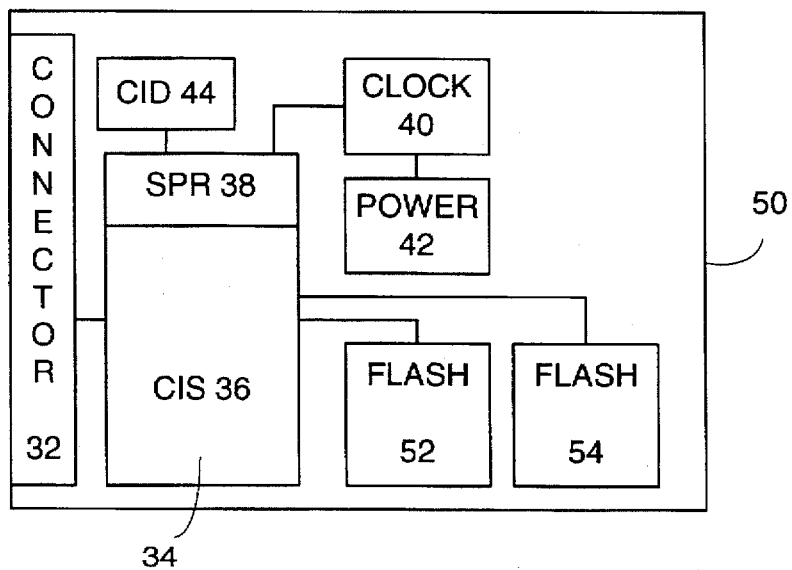

FIGS. 3 and 4 show suitable patient data cards for use with the defibrillator shown in FIG. 2. Data cards 30 and 50 are preferably in the 1995 PC Card standard format, with two key changes from the 1995 PC Card guidelines, as discussed below. It should be understood, however, that other digital memory formats may be used, such as the Minicard format promoted by Intel, Microsoft and others.

Data cards 30 and 50 each have a card connector 32 communicating with a gate array 34 over suitable buses. Gate array 34 contains the data card's Card Information Structure (CIS) 36 following the attribute memory of the 1995 PC Card guidelines. In addition, however, gate array 34 contains eight special purpose registers (SPR) 38.

Seven of the SPR 38 communicate with a clock 40, such as the elapsed time counter (ETC) chip clock 40 DS 1602, available from Dallas Semiconductor. Clock 40 preferably has a 32-bit elapsed time counter which begins counting when power is first provided to the clock's battery back-up pin from on-card battery 42 (i.e., when the card is first assembled). The counter increments once each second. Battery 42 is preferably a lithium battery.

Figure 5:
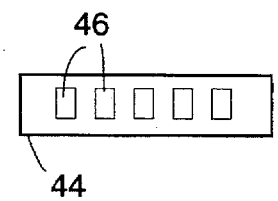
FIG. 5 is a schematic representation of a preferred form of card identification source (CID).

One of the SPR 38 communicates with the card identification (CID) source 44. CID 44 provides information about the card, such as type of memory on the card, size of memory on the card, data format, presence or absence of readable data (such as executable code), etc. In a preferred embodiment, CID 44 is a series of coding resistors 46, as shown schematically in FIG. 5, which can be read through gate array 34. Unique combinations of the coding resistors (i.e., whether a given resistor is "loaded" or not "loaded") identify the data card as a recording memory unit, (such as patient data card for storing patient and defibrillator information), an executing memory unit (such as a data card containing executable code for operating the defibrillator), or any other type of data card that the device is designed to use. Other ways of distinguishing one type of data card from another may be used, of course, without departing from the scope of the invention, such as DIP switches, binary code stored in memory locations, or other binary representation.

Data cards 30 and 50 differ in the kind of digital memory they provide. Data card 30 has an SRAM chip 43, while data card 50 has two substantially identical FLASH memory chips 52 and 54. Other combinations of memory, and other kinds of electrically-erasable and programmable nonvolatile memory, are within the scope of the invention.

Figure 6:
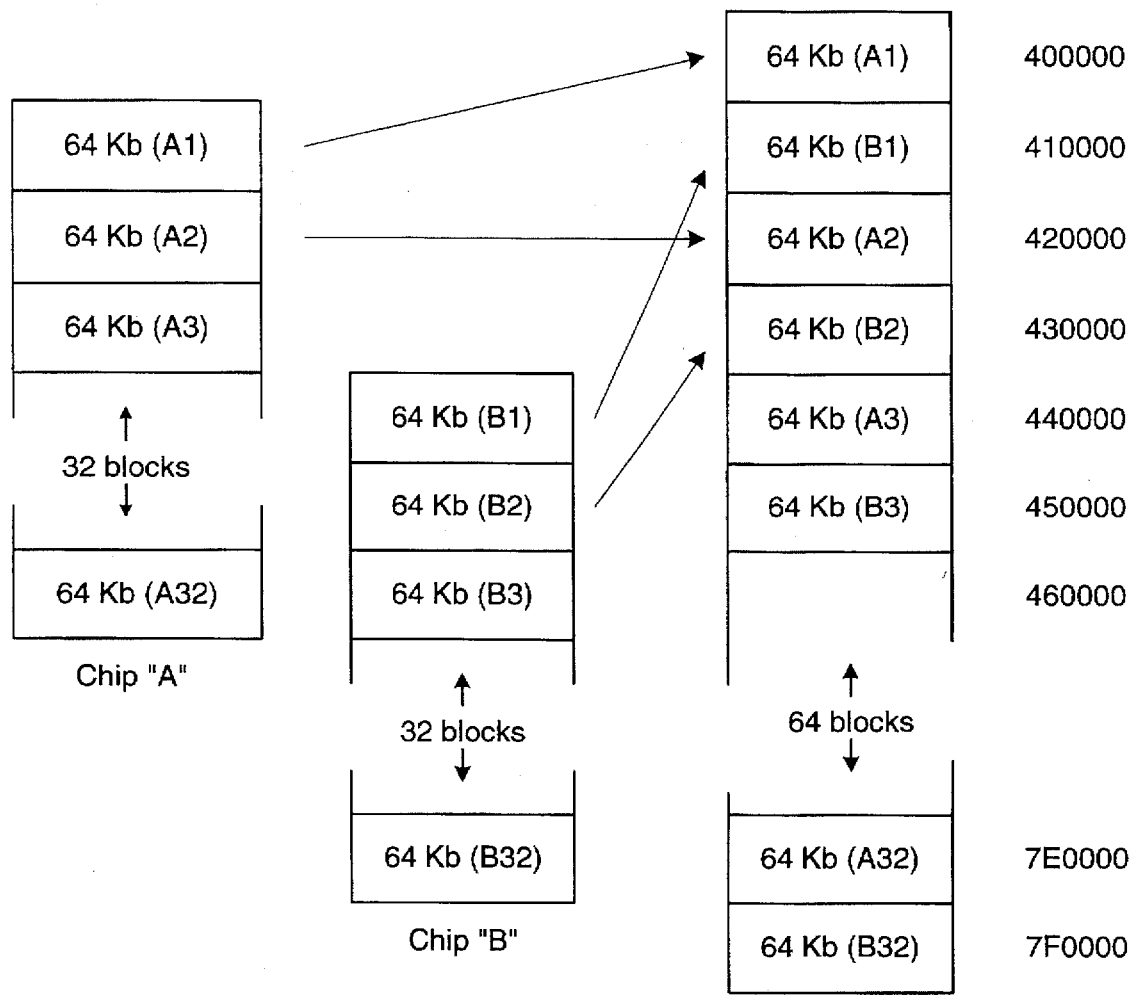
FIG. 6 shows an interleaving memory scheme for memory in a data card.

In the case of data card 50, both memory chips 52 and 54 are either top boot or bottom boot chips, although this is not necessary. In the preferred embodiment, the FLASH memory array is interleaved in a unique way to support an erase-on-the-fly scheme in a linear memory array. For example, for 16 Mbit chips having 32 64 Kbyte erase blocks, no data may be written to any block if another block in that chip is currently being erased. Since a block erase can take several seconds, an erase-on-the-fly scheme would require write suspends of up to several seconds each time a new block in the same chip is erased. To overcome this situation while preserving a linear memory array, data card 50 uses two 16 Mbit chips to form a 4 Mbyte linear array with interleaved 64 Kbyte blocks, i.e., the first 64 Kbyte block in a linear memory map is in one 16 Mbit chip (e.g., chip 52), the next is in the other chip (54), and so on. Thus, an application may erase a 64 Kbyte block immediately ahead of the one currently being accessed. FIG. 6 illustrates this scheme.

External defibrillator 100 can be operated in different modes, such as self-test mode, stand-by mode and patient treatment mode. Operation of the external defibrillator of this embodiment commences with the insertion of a battery. Once gate array 106 determines that a battery has been inserted to provide power to the defibrillator, gate array 104 prompts MPU 102 to begin its boot sequence. The boot sequence begins with MPU 102 sending out a series of addresses to gate array 104. Unless given instructions to the contrary, the initial MPU addresses to gate array 104 lead MPU to system ROM 114 for the remaining boot sequence.

The defibrillator's initial operation mode when booting from system ROM 114 is self-test mode during which the defibrillator performs an array of self-tests responding to insertion of the battery and possibly to the passage of time or an environmental event. Successful performance of these self-tests places the defibrillator in stand-by mode. The battery insertion self-tests may be terminated before completion by actuating on/off button 130, in which case the defibrillator's displayed status is determined by a shortened self-test sequence.

In stand-by mode, gate array 106 monitors for the presence of system power, the passage of time, temperature or other criteria. Gate array 106 places the defibrillator back into self-test mode when dictated by the passage of a suitable length of time, environmental conditions or other criteria. Failure of a self-test may cause the gate array 106 to place the defibrillator in an inoperable mode, in which case gate array indicates the inoperable status of the defibrillator through status display 128 and possibly other means. As stated above, the self-test results may be stored as time-correlated event data in system memory and/or in data card 117. In addition, environmental conditions--whether or not they trigger a self-test--may be recorded as event data as well.

When defibrillator 100 is in stand-by mode, actuation of on/off button 130 causes MPU 104 to begin receiving instructions from system ROM 114 to operate the defibrillator in a mode dictated by the instructions present in ROM 114. For example, provided that suitable instructions are present in ROM 114, actuation of on/off button 130 will place defibrillator 100 in patient treatment mode after successful completion of the defibrillator's power-on self-tests.

In patient treatment mode, defibrillator 100 can (1) determine whether electrodes are attached to electrode connector 136, (2) receive ECG information from a patient through such electrodes 137, (3) analyze the ECG information to determine whether a therapeutic shock is advised, and (4) deliver a shock to the patient through the electrodes if a shock is advised and if the shock button 126 is actuated by a user. Defibrillator 100 can also store information regarding the patient (such as ECG information), the defibrillator (such as defibrillator operation information) and other information (such as ambient sounds received by microphone 122) on a patient data card attached to data card port 116.

In the preferred embodiment, time information corresponding to all recorded event data comes from (1) defibrillator clock 107 and/or (2) the clock on the data card or other memory device. The following discussion illustrates the correlation of time information with event data collected during patient treatment mode. The invention covers the recording and time-correlation of other event data as well.

The event data collected by an external defibrillator (such as the defibrillator of FIG. 2) in patient treatment mode according to a preferred embodiment of this invention include the following: defibrillator power on; defibrillation pads on or off; patient ECG; artifact detection; shock advised; no shock advised; charge begun; charge complete; device armed; device disarmed; shock initiated; shock delivered; shock aborted; pause for CPR; pause ended; manual override; manual charge; manual timeout; device off; low battery; depleted battery; critical error detected; non-critical error detected; audio (e.g., voice). The defibrillator obtains time information from the defibrillator clock and/or the on the memory device and stores the time information with the event data.

As a specific example, when using the defibrillator of FIG. 2 and one of the data cards of FIGS. 3 or 4 to record this information and to provide the time information, the recording process begins when the defibrillator is turned on. At this time, the defibrillator records in data card digital memory (SRAM 44 or FLASH 52 or 54) a DEVICEON time from the continuous counter in clock 40. At the same time, the defibrillator starts a software counter associated with clock 107. In a New Use (i.e., when data begins recording at the beginning of the data card), ECG data is recorded after defibrillation electrodes or pads are attached to the patient and existing ECG memory on the card is erased. When the first ECG data point is recorded, a time RECORDTIME (derived from the software counter) is written to the data card memory. The ECG data is recorded and stored in data card memory at a resolution of 200 data points per second.

The recorded ECG data points (EDBT) are numbered, with the New Use having an EDBT of zero. With the exception of audio (e.g., voice) data, which start prior to ECG collection, all other event data stored in data card memory are correlated or stamped with the number of the ECG data point associated most closely with it in time. This technique provides finer correlation between ECG and other event data than the data card clock (with a resolution of only 1 sec.) can provide. The correspondence of the event data to clock time can easily be computed from RECORDTIME and the EDBT value.

After the defibrillator has been used to treat a patient and the time-correlated event data has been recorded, the memory device (e.g., data card) can be detached from the defibrillator and transported to a main data recovery unit (such as a PC) at another location. The clock on the data card will permit synchronization of the time-correlated event data with a clock in the main data recovery unit.

In addition to the event data collected and recorded automatically, the invention also provides for manual recording of event data.

This invention can be used to record other electrotherapy device event data, such as device history records. Device history records could include self-test results, number of shocks delivered during patient treatment use, amount of time the device was used in a particular use mode, etc.

Other modifications will be apparent to those skilled in the art.

What is claimed is:

1. A method of operating an electrotherapy device comprising the following steps:
   using the electrotherapy device to collect electrotherapy information;
   using a clock in the memory device to associate time information with the electrotherapy information; and
   storing the electrotherapy information and the time information on a detachable memory device.

2. The method of claim 1 wherein the step of using the electrotherapy device to collect electrotherapy information comprises collecting electrotherapy information automatically.

3. The method of claim 1 wherein the step of using the electrotherapy device to collect electrotherapy information comprises entering electrotherapy information manually.

4. The method of claim 1 wherein the storing step comprises storing the information on a PC data card.

5. The method of claim 1 further comprising, prior to the storing step, identifying a detachable memory device attached to the electrotherapy device, the storing step comprising storing the electrotherapy information and the time information on the detachable memory device.

6. The method of claim 1 wherein the memory device comprises a digital memory, the method comprising erasing a section of the digital memory prior to the storing step.

7. The method of claim 1 wherein the memory device comprises first and second digital memories, the method comprising erasing the first digital memory and the storing step comprising storing electrotherapy information and time information in the second digital memory during the erasing step.

8. The method of claim 1 further comprising using a clock in the electrotherapy device to associate time information with the electrotherapy information.

9. An electrotherapy system comprising:
   an electrotherapy device, the electrotherapy device comprising a memory device port; and
   a memory device, the memory device comprising a connector adapted to be connected to the electrotherapy device memory port, a clock, and a digital memory.

10. The electrotherapy system of claim 9 wherein the electrotherapy device further comprises means for using the clock to associate time information with electrotherapy information collected by the electrotherapy device.

11. The electrotherapy system of claim 9 wherein the memory device further comprises an identifier, the electrotherapy device further comprising means for identifying a memory device connected to the memory port.

12. The electrotherapy device of claim 9 wherein the digital memory is a first digital memory, the memory device further comprising a second digital memory, the electrotherapy device further comprising means for erasing the first digital memory while storing electrotherapy information and time information in the second digital memory.

* * * * *